(12) United States Patent
Jakatdar et al.

(10) Patent No.: US 6,743,646 B2
(45) Date of Patent: Jun. 1, 2004

(54) BALANCING PLANARIZATION OF LAYERS AND THE EFFECT OF UNDERLYING STRUCTURE ON THE METROLOGY SIGNAL

(75) Inventors: Nickhil Jakatdar, Los Altos, CA (US); Xinhui Niu, San Jose, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 49 days.

(21) Appl. No.: 10/035,925

(22) Filed: Oct. 22, 2001

(65) Prior Publication Data
US 2003/0194820 A1 Oct. 16, 2003

(51) Int. Cl.[7] .................. H01L 21/66; G01R 31/26
(52) U.S. Cl. .................. 438/16; 438/14; 438/15; 438/17; 438/18; 356/364; 356/369; 356/445; 324/765
(58) Field of Search ................ 356/364, 369, 356/445; 324/765; 438/14–18

(56) References Cited

U.S. PATENT DOCUMENTS

| | | | | |
|---|---|---|---|---|
| 4,855,253 A | * | 8/1989 | Weber | 438/18 |
| 5,717,490 A | * | 2/1998 | Kumar | 356/630 |
| 5,739,909 A | * | 4/1998 | Blayo et al. | 356/369 |
| 5,835,225 A | | 11/1998 | Thakur | |
| 6,015,718 A | * | 1/2000 | Rathbone | 438/17 |
| 6,072,191 A | * | 6/2000 | La et al. | 257/48 |
| 6,146,910 A | * | 11/2000 | Cresswell et al. | 438/14 |
| 6,263,255 B1 | | 7/2001 | Tan et al. | |
| 6,297,880 B1 | * | 10/2001 | Rosencwaig et al. | 356/369 |
| 6,298,470 B1 | | 10/2001 | Breiner et al. | |
| 6,309,900 B1 | * | 10/2001 | Maury et al. | 438/16 |
| 6,347,291 B1 | * | 2/2002 | Berman | 702/150 |
| 6,484,064 B1 | | 11/2002 | Campbell | |

\* cited by examiner

*Primary Examiner*—Ernest Karlsen
*Assistant Examiner*—Lisa Kilday
(74) *Attorney, Agent, or Firm*—Morrison & Foerster LLP

(57) ABSTRACT

One embodiment of the present invention is a method of designing underlying structures in a wafer with pads of varying sizes and varying loading factors, and selecting the design of pads that yield a reflected metrology signal closest to the calibration metrology signal and that meet preset standard planarization characteristics. Another embodiment is a method of designing underlying structures with random shapes of varying sizes and varying loading factors. Still another embodiment is the use of periodic structures of varying line-to-space ratios in one or more underlying layers of a wafer, the periodicity of the underlying periodic structure being positioned at an angle relative to the direction of periodicity of the target periodic structure of the wafer.

20 Claims, 10 Drawing Sheets

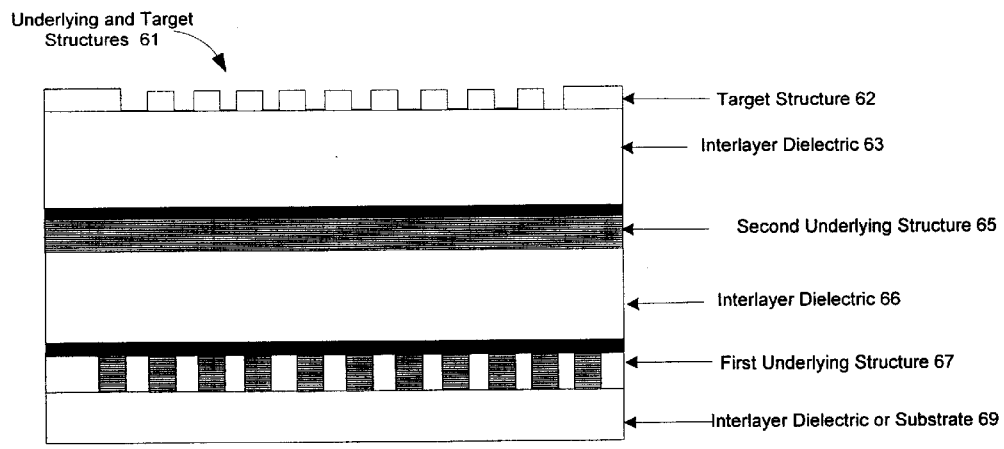
FIGURE 3A
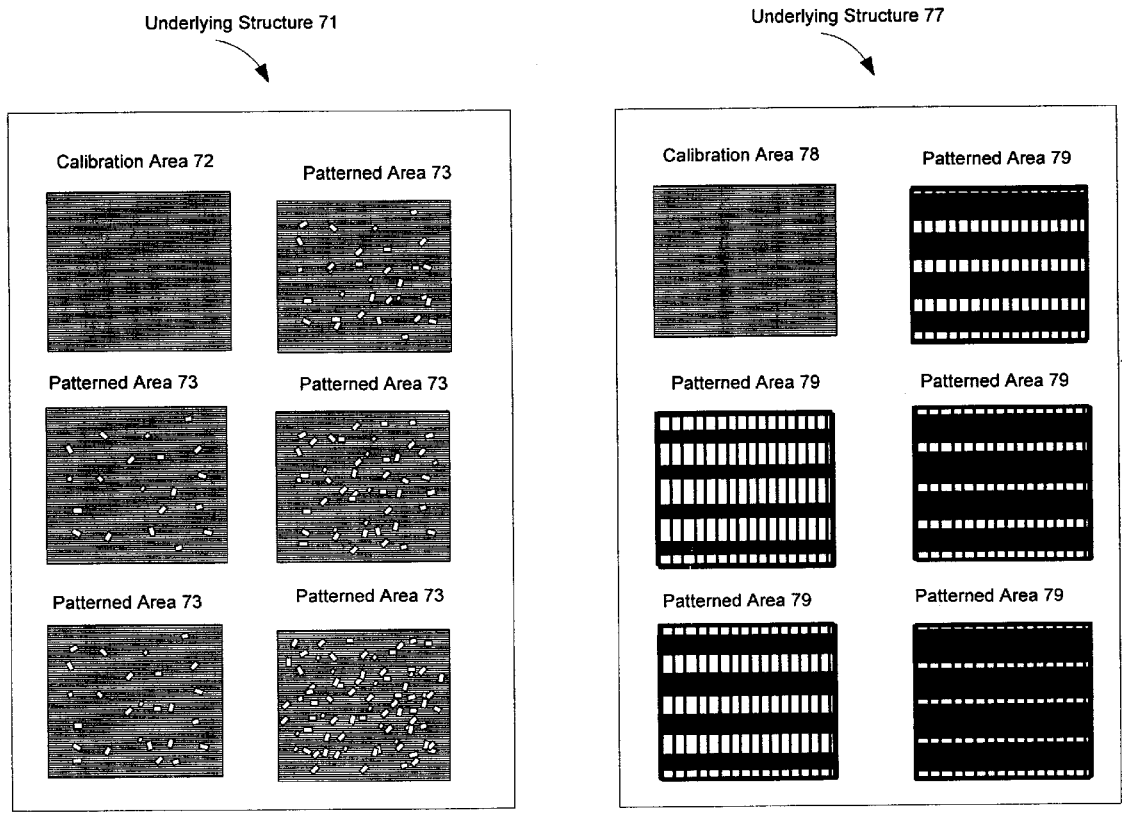
FIGURE 3B
FIGURE 3C

BALANCING PLANARIZATION OF LAYERS AND THE EFFECT OF UNDERLYING STRUCTURE ON THE METROLOGY SIGNAL

BACKGROUND OF INVENTION

1. Field of Invention

This invention is in the field of manufacture of semiconductor devices. More particularly, this invention relates to a method and system of fabricating underlying structures to improve planarization characteristics of layers while minimizing introduction of random and/or systematic noise by the underlying structures to the metrology signal.

2. Related Art

As feature sizes in semiconductor devices shrink, photolithographic equipment requires that layers of a wafer be very flat or planar so that small feature dimensions are accurately patterned. Chemical mechanical planarization (CMP) is widely used in various semiconductor processing operations to planarize layers of a wafer. The polishing process typically uses an abrasive slurry and a combination of mechanical and chemical actions to planarize the layer surface.

CMP performance is affected by the density of underlying structures in a wafer, resulting in two phenomena called "dishing" and "erosion". FIG. 1A is an architectural diagram illustrating the "dishing" effects of the CMP process on a layer of a wafer. In a stacked wafer structure 13, the stack comprises a silicon layer or a substrate 11 and a dielectric layer or layers 9, a metal seed layer 7, and an interlayer dielectric (ILD) 5, typically silicon oxide. The metal layer 3, typically copper, aluminum, or tungsten, is planarized using a CMP process. Since the metal layer 3 is relatively softer than the ILD plus the chemical action of the CMP, a metal loss region 1 occurs, referred to as "dishing".

FIG. 1B is an architectural diagram illustrating the "erosion" effects of the CMP process on a layer of a wafer. In a stacked wafer structure 20, an ILD layer 31 is fabricated above a substrate or previous layers (not shown). Another ILD layer 25 is fabricated above the etch stopper layer 29. The metal layer 23 is planarized using a CMP process where a different polishing rate applies to the dense region 24 compared to the region with small features 22. The difference in the polishing rate is most pronounced in the middle of the small feature region 22, resulting in a concave-profile loss region consisting of loss of ILD and metal. This phenomenon, referred to as "erosion".

One of the solutions used to solve the local pattern density effect is to use fill or dummy shapes. U.S. Pat. No. 5,278,105 entitled "Semiconductor Device with Dummy Features in Active Layers" to Eden, et al., discusses the use of fill shapes for correcting problems related to local pattern density FIG. 2 is an architectural diagram illustrating the use of an optical metrology system to acquire critical dimension (CD) data off target periodic structures. The optical metrology system 40 consists of a metrology beam source 41 projecting a beam 43 at the target periodic structure 53 of a wafer, 43 mounted on a metrology platform 55. The metrology beam 43 is projected at an incidence angle θ towards the target periodic structure 53. The reflected beam 49 is measured by a metrology beam receiver 51. The reflected beam data 57 is transmitted to a metrology profiler system 53. The metrology profiler system 53 compares the measured reflected beam data 57 against a library of calculated reflected beam data representing varying combinations of critical dimensions of the target periodic structure and resolution. The library instance best matching the measured reflected beam data 57 is selected. The profile and associated critical dimensions of the selected library instance correspond to the cross-sectional profile and critical dimensions of the features of the target periodic structure 53. A similar optical metrology system 40 is described in U.S. Pat. No. 5,739,909, entitled "Measurement and Control of Linewidths in Periodic Structures Using Spectroscopic Ellipsometry.", issued to Blayo, et al.

Two spectroscopic metrology techniques are used typically to measure target structures in a non-destructive manner: spectroscopic reflectometry and spectroscopic ellipsometry. In reflectometry, light intensities are measured. $R=|r|^2$ is the relation between the reflectance R and the complex reflection coefficient r. In spectroscopic ellipsometry, the component waves of the incident light, which are linearly polarized with the electric field vibrating parallel (p or TM) or perpendicular (s or TE) to the plane of incidence, behave differently upon reflection. The component waves experience different amplitude attenuations and different absolute phase shifts upon reflection; hence, the state of polarization is changed. Ellipsometry refers to the measurement of the state of polarization before and after reflection for the purpose of studying the properties of the reflecting boundary. The measurement is usually expressed as tangent ($\Psi$) and cosine ($\Delta$).

In spectroscopic metrology, the reflected optical signal is considered ideal when the underlying structure is unpatterned, i.e., like a unpatterned film or substrate. The presence of a pattern in the underlying structure may introduce random and/or systematic noise to the measured reflected optical signal. The source of random noise cannot be determined whereas systematic noise can possibly be determined and characterized. Significant random or systematic noise in the signal in turn skews the matching process of the measured reflected signal against the library of calculated reflected beam data, causing the match of the measured reflected signal to a different profile and/or different critical dimensions.

On the other hand, the underlying structure design may not introduce random and/or systematic noise to the measured reflected optical signal but the CMP characteristics of planarized layers might exceed ranges required by the application.

Thus, there is a need for identification of an underlying structure that achieves improved planarization characteristics of layers while minimizing introduction of random and/or systematic noise to the reflected metrology signal.

SUMMARY OF INVENTION

The present invention is a method and system for identifying an underlying structure that achieves improved planarization characteristics of layers while minimizing introduction of random and/or systematic noise to the reflected metrology signal.

One embodiment of the present invention is a method of optimizing the design of underlying structures in a wafer with one or more designs of pads of varying sizes and varying loading factors, comparing planarization characteristics of the underlying layers of the wafer to preset standard planarization characteristics, fabricating target structures in the target layer of the wafer, measuring a reflected metrology signal off a calibration test area to obtain a calibration metrology signal, the calibration test area having an unpatterned underlying structure, and selecting the design of pads that yield a reflected metrology signal closest to the calibration metrology signal and that meet preset standard planarization characteristics. Another embodiment is a method of designing underlying structures with one or more designs of random shapes of varying sizes and varying loading factors in underlying layers of a wafer.

Still another embodiment of the present invention is a method of optimizing the design of underlying structures with one or more periodic structures of varying line-to-space ratios in one or more underlying layers of a wafer, the periodicity of the underlying periodic structure being positioned at an angle relative to the direction of periodicity of the target periodic structure of the wafer. In one application, the angle relative to the direction of periodicity of the target periodic structure of the wafer is ninety degrees.

The present invention also includes a system for optimizing the selection of an underlying structure design that balances planarization and optical metrology objectives for a target structure comprising a wafer fabricator, a planarizer for planarizing a surface of an underlying layer of the wafer, a layer profiler for measuring the planarization characteristics of planarized layers of the wafer, an optical metrology device for processing the reflected signal from the target structure in the target layer of the wafer, and a selector for the selecting the design of underlying structure that yields a reflected metrology signal closest to the calibration metrology signal and that meets preset standard planarization characteristics.

BRIEF DESCRIPTION OF DRAWINGS

FIG. 3A is an architectural diagram illustrating the target structures, underlying structures, and interlayer dielectric, in one embodiment of the present invention.

FIG. 3B is an architectural diagram illustrating a top view of an underlying structure showing a calibration area and patterned areas with random shapes.

FIG. 3C is an architectural diagram illustrating a top view of an underlying structure showing a calibration area and patterned areas with periodic structures.

DETAILED DESCRIPTION OF EXEMPLARY EMBODIMENT(S)

The present invention includes a method for identifying, for a given target structure, the design, distribution, and density of fill shapes of the underlying structures and/or the arrangement of the patterned underlying structures that will minimize the introduction of random or systematic noise to the reflected metrology signal off the target structure.

Figure 8:
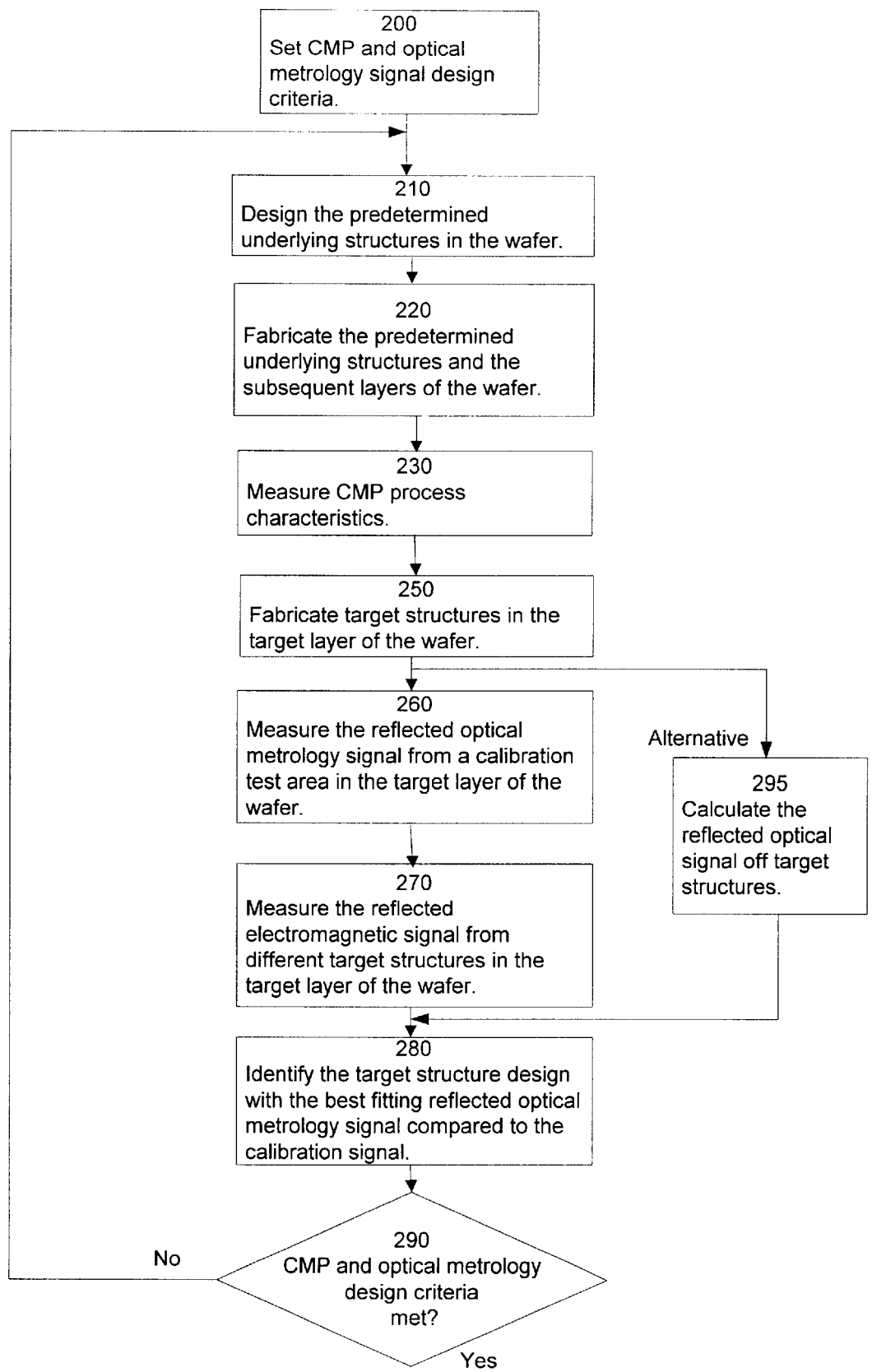
FIG. 8 is flow chart of operational steps of one embodiment of the present invention.

A summary of the process for the present invention, described in detail in FIG. 8, is provided here to facilitate the descriptions of figures that follow. Initially, the CMP and optical metrology signal design criteria for the target structure are set. A target structure is the patterned structure of a layer of a wafer that is measured using optical metrology. A predetermined set of underlying structures, including a calibration underlying structure, is designed. Based on the CMP design criteria, a set of pads and/or random shapes of varying size, geometry, and loading factors may be designed in a mask for the underlying structures. Alternatively, a set of periodic underlying structures with varying line-to-space ratios may be designed. The predetermined set of underlying structures and subsequent layers of the wafer are fabricated. A CMP process may be required for one or more of the subsequent layers of the wafer. Whenever a CMP process is involved, the CMP process characteristics of the planarized layer are measured. The target structures in the target layer of the wafer are fabricated. The reflected optical; metrology signal from a calibration test area in the target layer of the wafer is measured. Once the calibration reflected optical metrology signal is obtained, reflected optical metrology signals from the other target structures with underlying structures varying in either loading factors or line-to-space ratios are measured.

In an alternative embodiment for periodic underlying structures, the reflected optical metrology signals from the target structures in the target layer may be calculated for both the calibration test area and the other test structures with underlying structures varying in either loading factors or line-to-space ratios. The measured or the calculated reflected optical metrology signals are compared to the calibration reflected optical metrology signal and the best-fitting measured or calculated reflected optical metrology signal is identified. If both of the CMP and optical metrology signal design criteria are met, the underlying structure associated with the target structure identified as having best-fitting signal is selected as the underlying structure for the fabrication run. Otherwise, the process is iterated starting with designing a new set of underlying structures.

Figure 1A:
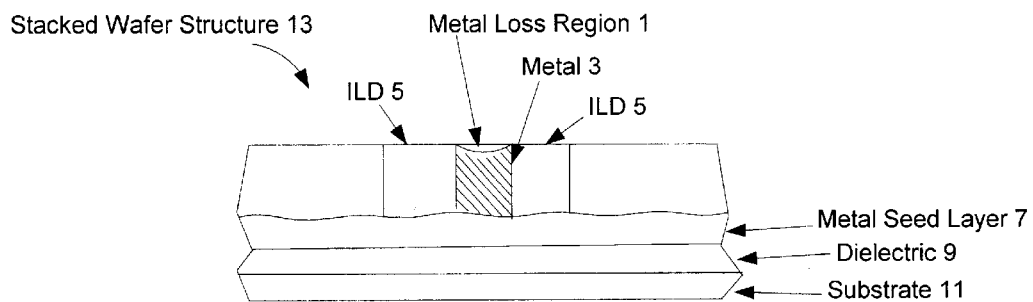
FIG. 1A is an architectural diagram illustrating the "dishing" effects of the CMP process on a layer of a wafer.
Figure 1B:
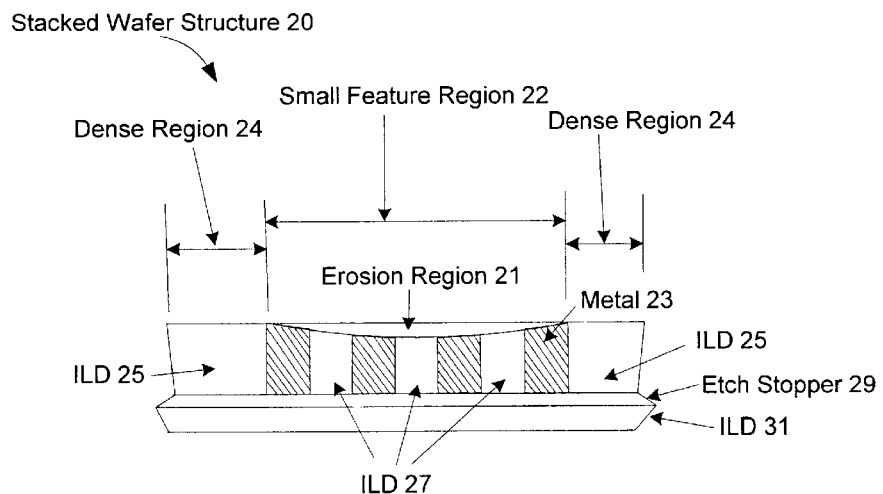
FIG. 1B is an architectural diagram illustrating the "erosion" effects of the CMP process on a layer of a wafer.
Figure 2:
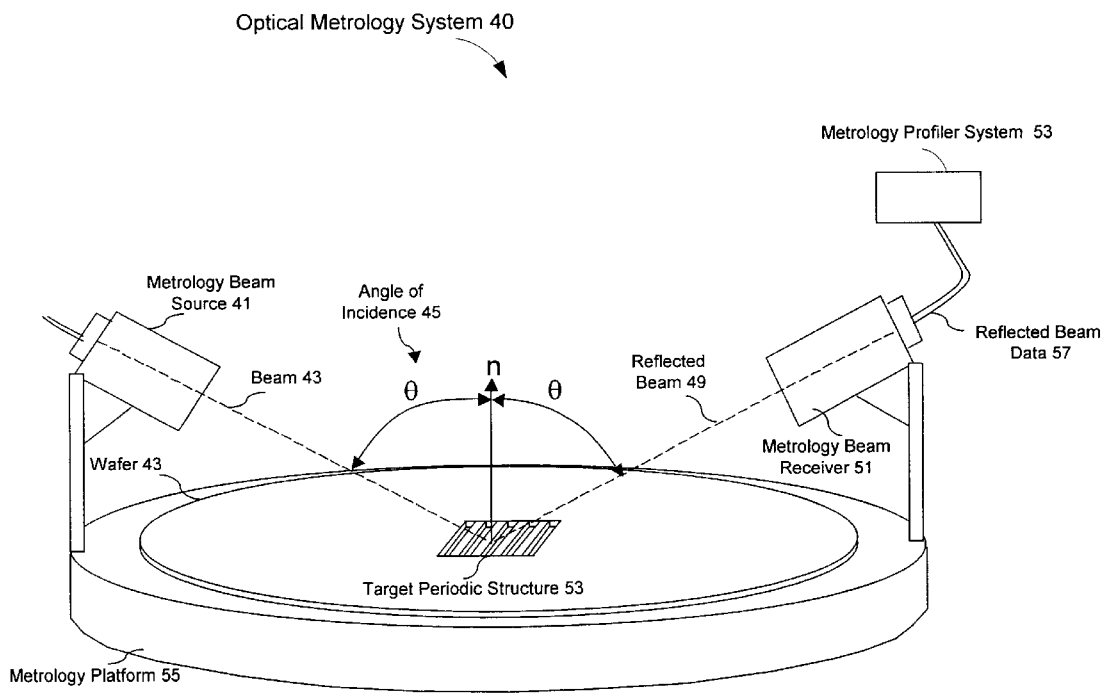
FIG. 2 is an architectural diagram illustrating the use of an optical metrology system to acquire critical dimension (CD) data off target periodic structures.

FIG. 3A is an architectural diagram illustrating the target structures, underlying structures, and interlayer dielectric in one embodiment of the present invention. The first underlying structure 67 is fabricated above an interlayer dielectric (ILD) or substrate 69. The second underlying structure 65 is fabricated on top of the first underlying structure 67 with an ILD 66 in between. The target structure 62 is fabricated over one or more ILD's 63. The critical dimensions and profile of features of the target structure 62 in the target layer is measured with an optical metrology device, (not shown), such as the one depicted in FIG. 2.

FIG. 3B is an architectural diagram illustrating a top view of an underlying structure showing a calibration area and patterned areas with random shapes. The calibration area 72 is unpatterned whereas the patterned areas 73 have different designs, distribution, and density of fill shapes. An optical metrology device is used to measure the reflected metrology signal off the target structure above the calibration area 72. This calibration reflected metrology signal is the baseline for comparing the measured reflected optical metrology signals off the target structure above the patterned areas 73.

Similarly, FIG. 3C is an architectural diagram illustrating a top view of an underlying structure showing a calibration area and patterned areas with periodic structures. The calibration area 78 is unpatterned whereas the patterned areas 79 have different line-to-space ratios. An optical metrology device is used to measure reflected metrology signal off the target structure above the calibration area 78. This calibration reflected metrology signal is the baseline for comparing the measured reflected optical metrology signals off the target structure above patterned areas 79.

Figure 4A:
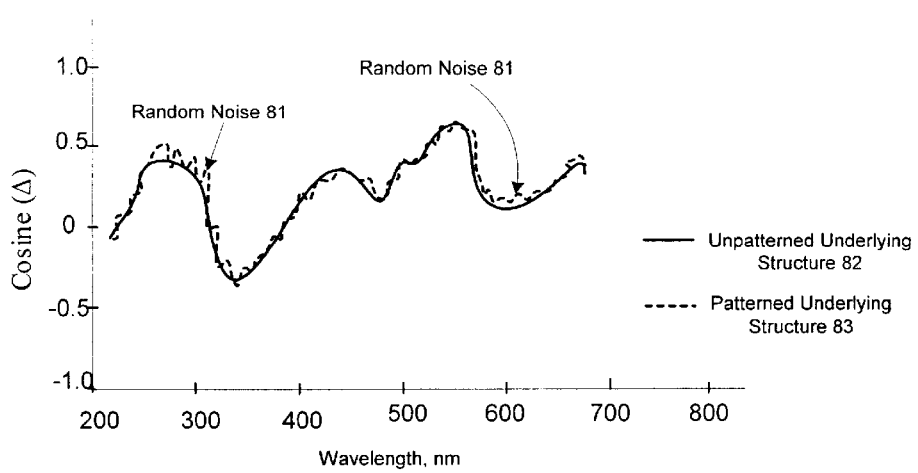
FIG. 4A is a graph illustrating random noise introduced in metrology measurements due to patterns in the underlying structure.

FIG. 4A is a graph illustrating random noise introduced in metrology measurements due to patterns in the underlying structure. The X-axis is the wavelength in nanometers while the Y-axis is cosine ($\Delta$). The solid line graph 82 is the calculated or measured reflected calibration metrology signals off the target structure with an unpatterned underlying structure and shows the variation of cosine ($\Delta$) as a function of wavelength. Use of certain fill shapes to optimize the CMP characteristics of layers of the wafer introduces random noise 81 to the reflected metrology signal. The dotted line graph 83 of cosine ($\Delta$) is different from the solid line graph 82 of the calculated or measured reflected calibration metrology signals. As a result of the random noise, the measured reflected metrology signal for the patterned areas can have a different best-matching instance of the library of calculated reflected optical metrology data. Thus, the profile and associated critical dimensions of the target structure provided by optical metrology would be different as a result of random noise introduced by the underlying structure.

Figure 4B:
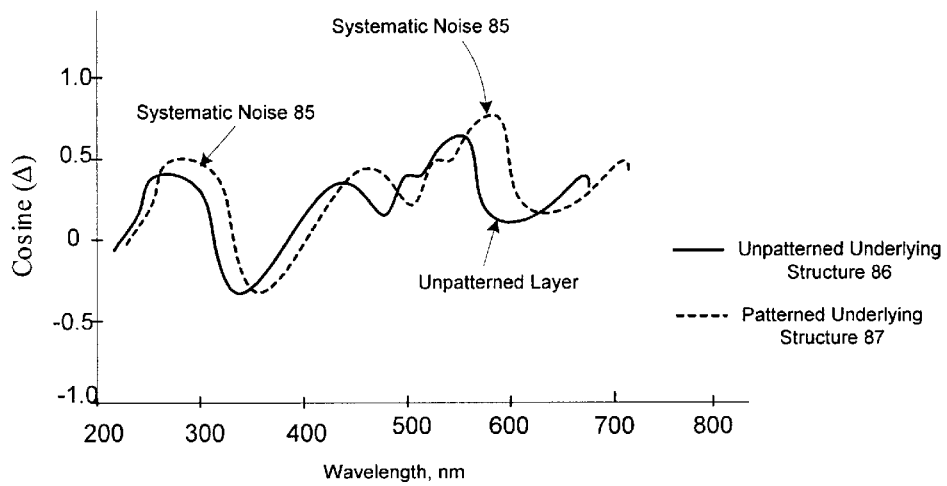
FIG. 4B is a graph illustrating systematic noise introduced in metrology measurements due to patterns in the underlying structure.

FIG. 4B is a graph illustrating systematic noise introduced in metrology measurements due to patterns in the underlying structure. Similar to FIG. 4A, the X-axis is the wavelength in nanometers while the Y-axis is cosine ($\Delta$). The solid line graph 86 is the calculated or measured reflected calibration metrology signals of the target structure with an unpatterned underlying structure. The dotted line graph 87 of cosine ($\Delta$) is different from the solid line graph 86 of the calculated or measured reflected calibration metrology signals. As a result of the systematic noise, the measured reflected metrology signal for the patterned areas would have a different best-matching instance of the library of calculated reflected optical metrology data. Thus, the profile and associated critical dimensions of the target structure provided by optical metrology would be different as a result of systematic noise introduced by the underlying structure.

Figure 4C:
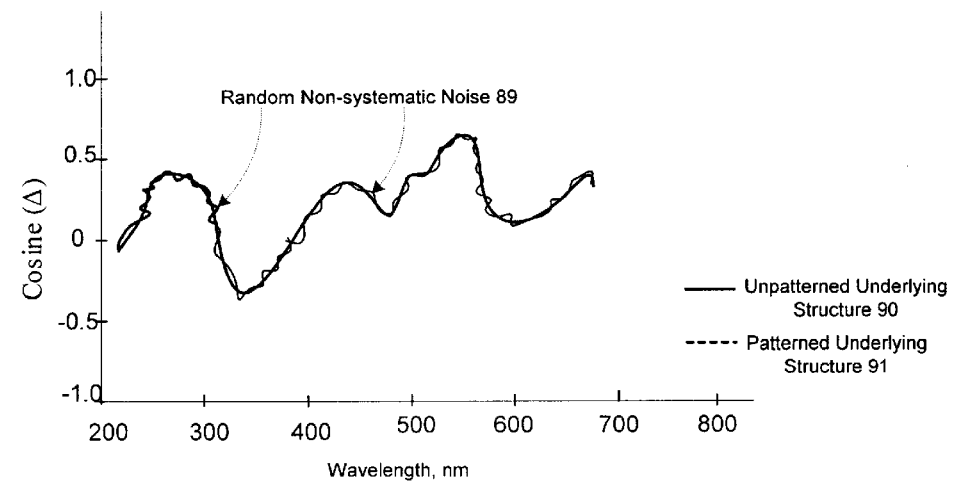
FIG. 4C is a graph illustrating significantly reduced random non-systematic noise in the metrology signal due to an underlying structure design that approximates the reflected metrology signal of an unpatterned underlying structure.

FIG. 4C is a graph illustrating significantly reduced random non-systematic noise in the metrology signal due to an underlying structure design that approximates the reflected metrology signal of an unpatterned underlying structure. Similar to FIG. 4A, the X-axis is the wavelength in nanometers while the Y-axis is cosine ($\Delta$). The solid line graph 90 is the calculated or measured reflected calibration metrology signals of the target structure with an unpatterned underlying structure. The underlying structures used to optimize the CMP characteristics of layers of the wafer resulted in significantly reduced random non-systematic noise 89 to the measured reflected metrology signal off the patterned underlying areas. The measured reflected metrology signal off the target structures with patterned underlying areas averages out to a graph that is close to the solid line graph 90. As a result, the best-matching instance of the library of calculated reflected optical metrology data to the measured reflected optical metrology data with patterned underlying areas would provide profile and associated critical dimensions that are acceptable for a given fabrication run.

For a given target structure and wafer fabrication process, the present invention identifies the design of an underlying structure that minimizes the introduction of random and/or systematic noise yet meets planarization objectives. As mentioned earlier, fill shapes, including pads or random shapes, may be used. For fill shapes, the key factor that integrates the effect of design, distribution, and density is the loading factor. Loading factor is the percentage of the area covered by the fill shapes compared to the total patterned area. The underlying structure may also be a periodic structure. The key factors in an underlying structure comprising periodic structures are the line-to-space ratio and angle between the periodicity of the underlying structure and the periodicity of the target structure or orientation.

Figure 5:
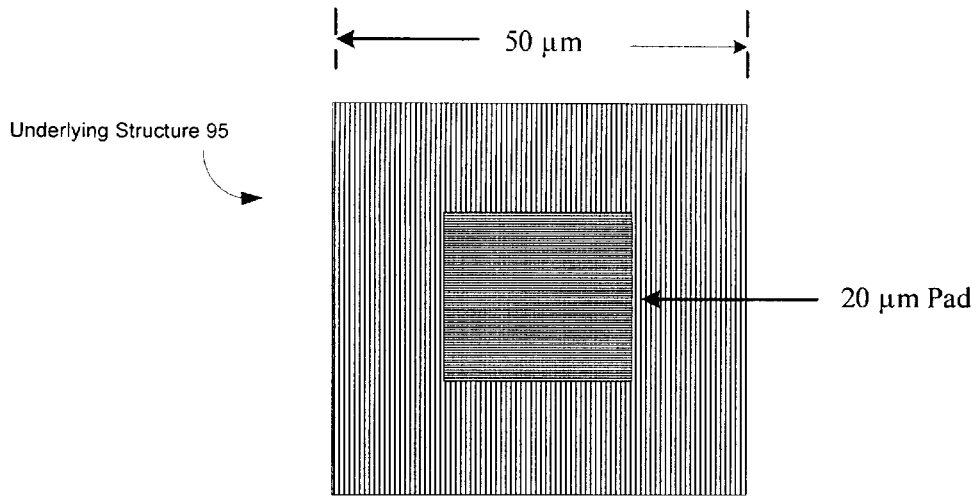
FIG. 5 is an architectural diagram illustrating the use of varying size pads for balancing the CMP effects and effects on the reflected optical metrology signal in one embodiment of the present invention.
Figure 5:
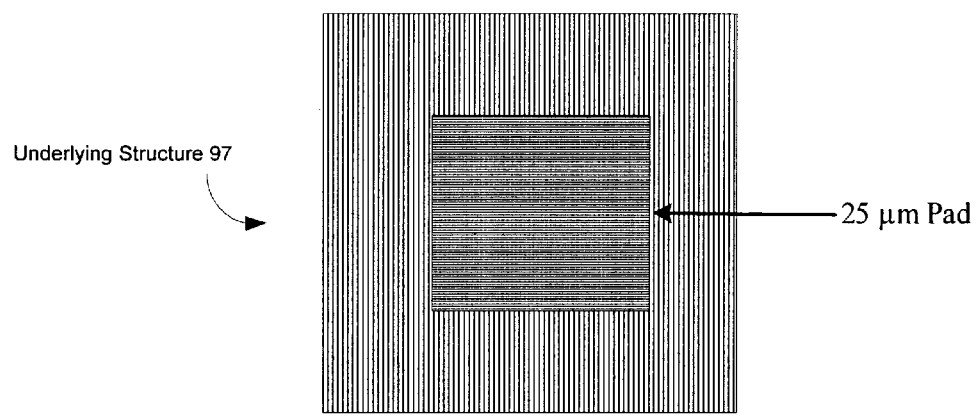
Figure 5:
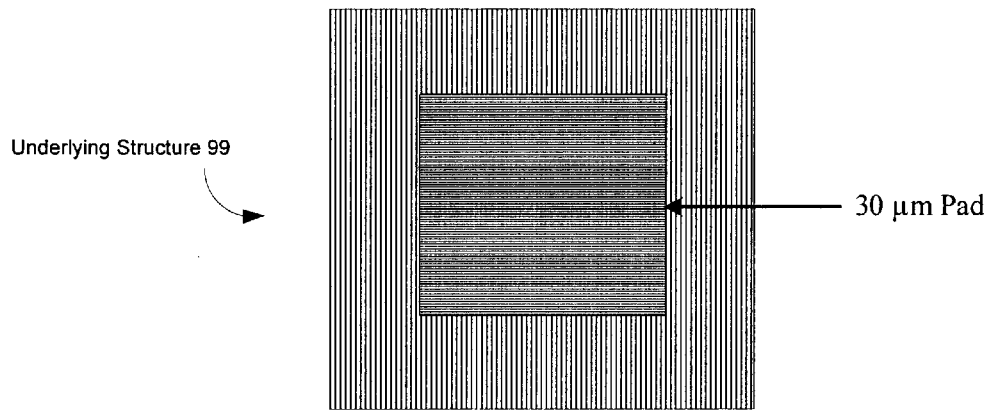

FIG. 5 is an architectural diagram illustrating the use of varying size pads for balancing the CMP effects and effects on the reflected optical metrology signal in one embodiment of the present invention. Fill shapes may be pads of any geometric configuration, such as squares, circles, or pentagons. FIG. 5 shows three square-shaped test underlying areas 95, 97, and 99 of 50 micrometers ($\mu$m) with varying sizes of pads, from 20 $\mu$m to 30 $\mu$m. The loading factors for the three pads are 16%, 25%, and 36% respectively. Loading factors may range from 1 to 100%. The present invention optimizes the loading factor for the particular target structure and fabrication process.

Figure 6:
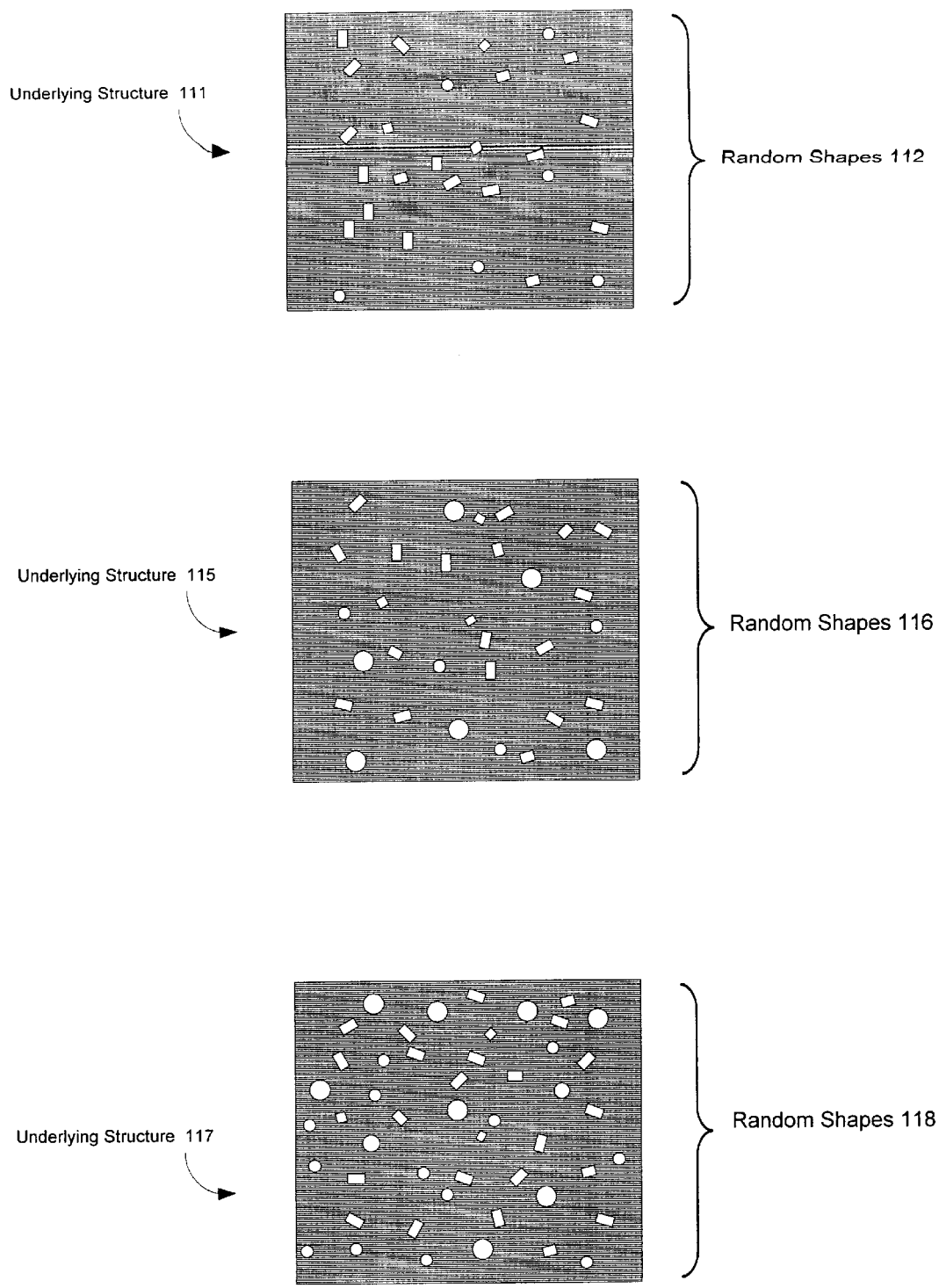
FIG. 6 is an architectural diagram illustrating the use of random shapes for balancing the CMP effects and effects on the reflected optical metrology signal in one embodiment of the present invention.

FIG. 6 is an architectural diagram illustrating the use of random shapes for balancing the CMP effects and effects on the reflected optical metrology signal in one embodiment of the present invention. The three square-shaped test underlying areas 111, 115, and 117 show the varying design, distribution and, densities of random shapes 112, 116, and 118. Again, the key factor is the loading factors of the different random shapes. Random shapes include geometric shape or non-geometric shapes such as "islands".

Figure 7A:
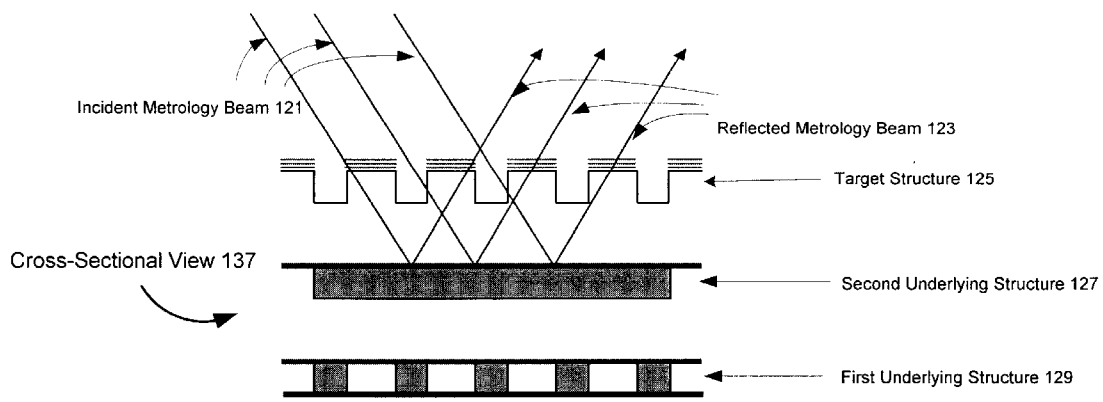
FIG. 7A is a cross-sectional view illustrating multi-layer underlying structures for a dual damascene target structure in one embodiment of the present invention.

FIG. 7A is a cross-sectional view illustrating multi-layer underlying structures for a dual damascene target structure in one embodiment of the present invention. The first underlying structure is a periodic structure where the direction of periodicity is the same as the direction of periodicity of the target structure 125. The second underlying structure 127 may be a simple pad, a group of random shapes, or a periodic structure whose direction of periodicity is perpendicular or substantially perpendicular to the direction of periodicity of the target structure 125. An incident metrology beam 121 is projected to the target structure 125 and the reflected metrology beam 123 is measured by a metrology device (not shown).

Figure 7B:
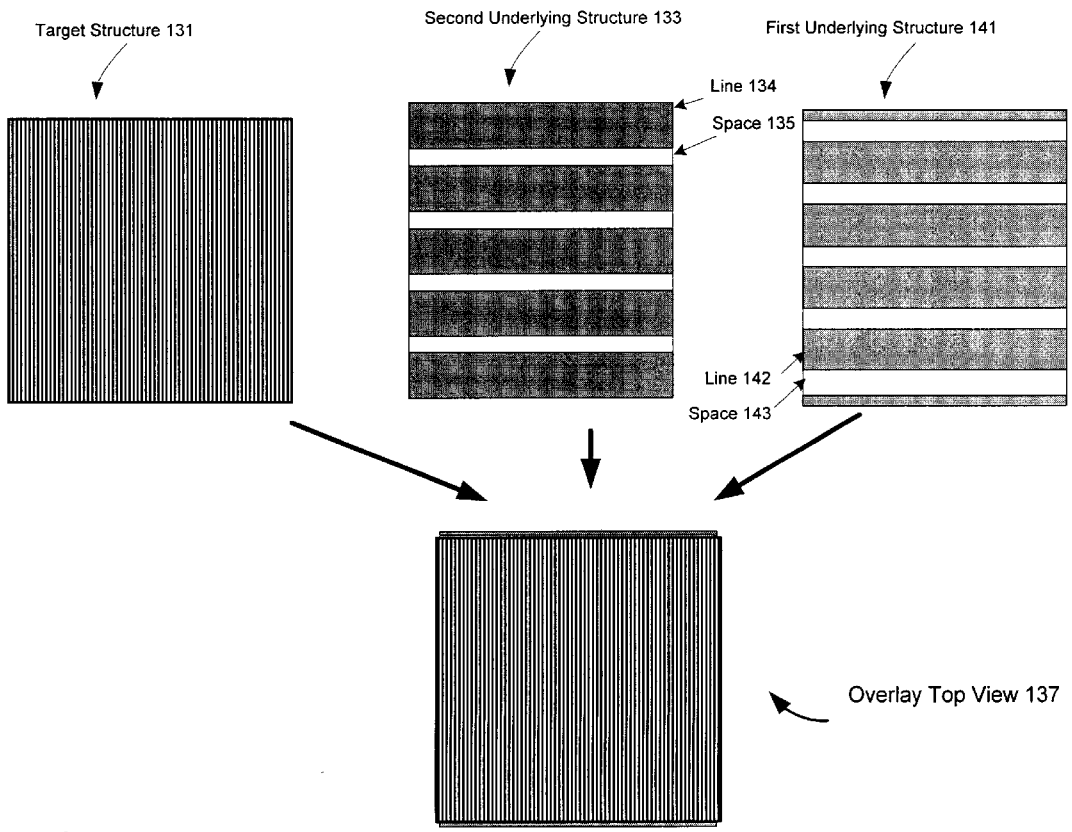
FIG. 7B is a top-view illustrating dual layer underlying structures perpendicular to the direction of periodicity of the target structure in one embodiment of the present invention.

FIG. 7B is a top-view illustrating dual layer underlying structures perpendicular to the direction of periodicity of the target structure in one embodiment of the present invention. The second underlying structure 133 is a periodic structure with the direction of periodicity perpendicular or substantially perpendicular to the direction of periodicity of the target structure 131. The second underlying structure 133 consists of lines 134 and spaces 135. Similarly, the first underlying structure 141 is also a periodic structure with the direction of periodicity perpendicular or substantially perpendicular to the direction of periodicity of the target structure 131, consisting of lines 142 and spaces 143. The lines 142 of the first underlying structure are directly under the corresponding spaces 135 of the second underlying structure 133. The width of lines 142 of the first underlying structure are sufficient to completely cover the width of the corresponding spaces 135 of the second underlying structure 133. This line-and-space arrangement of the first underlying structure 141 and the second underlying structure 133 reduces diffraction of the metrology beam (not shown). The key factors that minimize introduction of random and/or systematic noise to the reflected metrology signal are the line-to-space ratio of the first underlying structure 133 and angle between the periodicity of the underlying structures and the periodicity of the target structure.

FIG. 8 is flow chart of operational steps of one embodiment of the present invention. The CMP and optical metrology signal design criteria for the target structure are set 200. The design criteria depend on the target structure fabrication process and the application. For example, if the target structure is for an application that requires a high CMP standard, then the CMP design criteria may be stricter than an application that accepts a wider range of acceptable dishing and erosion in planarized layers. On the other hand, if a target structure is for an application where a specific profile and a very tight range of profile critical dimensions are required, then the optical metrology signal design criteria may be the controlling consideration. In one embodiment, the CMP design criteria may be stated in terms of angstroms or nanometers of acceptable dishing and/or erosion. The optical metrology signal design criteria may be expressed as percentage goodness-of-fit (GOF). GOF is the inverse of the error between the measured reflected metrology signal and the calibration measured reflected metrology signal, expressed as a percentage. The best matching measured reflected metrology signal is one with the least error compared to the calibration reflected metrology signal. Several optimization procedures are available to minimize the error, such as simulated annealing, described in "Numerical Recipes," section 10.9, Press, Flannery, Teulkolsky & Vetterling, Cambridge University Press, 1986; which is incorporated by reference. The error metric that produces appropriate results is the sum-squared-difference-log error, where the optimization procedure minimizes the error metric between the measured reflected metrology signal and the calibration reflected metrology signal.

A predetermined set of underlying structures, including a calibration underlying structure, is designed 210. Based on the design criteria, a set of pads and/or random shapes of varying size, geometry, and loading factors may be designed in a mask. Alternatively, a set of periodic underlying structures with varying line-to-space ratios may be designed. In one embodiment, the underlying structures may comprise of circular pads with loading factors from about fifty to about ninety five percent (50–95%). In an alternative embodiment, the underlying structure may comprise of two layers where the top layer is a periodic structure with line-to-space ratio of 0.10 to 0.60 and a bottom layer with line-to-space ratio of 0.10 to 0.60 with the bottom layer line centered below the corresponding top layer space. In still another embodiment for a periodic underlying structure, the angle between the periodicity of the underlying structures and the periodicity of the target structure is ninety degrees.

The predetermined set of underlying structures and subsequent layers of the wafer are fabricated 220. A CMP process may be required for one or more of the subsequent layers of the wafer. Whenever a CMP process is involved, the CMP process characteristics of the planarized layer are measured 230. In one embodiment, the extent of dishing and/or erosion in angstroms is measured. Other measures such as long-scan measurement of dishing, erosion, step height, and planarity may be used. In still other embodiments, micro-scratches, and/or three-dimensional mapping of flatness may be measured. Examples of devices capable of the aforementioned measurement are available from Digital Instruments, Veeco Metrology Group, KLA-Tencor, and other atomic force profiler manufacturers. The target structures in the target layer of the wafer are fabricated 250.

The reflected optical metrology signal from a calibration test area in the target layer of the wafer is measured 260. A calibration test area in the target layer of the wafer is one whose underlying structure is an unpatterned layer. Once the calibration reflected optical metrology signal is obtained, reflected optical metrology signals from the other target structures with underlying structures varying in either loading factors or line-to-space ratios are measured 270.

In an alternative embodiment for periodic underlying structures, the reflected optical metrology signals from the target structures in the target layer may be calculated 295 for both the calibration test area and the other test structures with underlying structures varying in either loading factors or line-to-space ratios. Calculations of reflected optical metrology signals may be done by a number of techniques. One calculation technique is the so-called rigorous coupled-wave analysis (RCWA). The details of an application of RCWA in calculating the reflected optical metrology signals is contained in co-pending U.S. patent application Ser. No. 09/770,997 entitled "Caching of Intra-Layer Calculations for Rapid Rigorous Coupled-Wave Analyses" by Niu, et al., filed on Jan. 25, 2001, owned by the assignee of this application, the entire content of which is incorporated herein by reference.

The measured or the calculated reflected optical metrology signals are compared to the calibration reflected optical metrology signal and the best-fitting measured or calculated reflected optical metrology signal is identified 280. In one embodiment, the best fitting signal is identified by GOF and the best fitting signal in this case is the underlying structure with the highest GOF. For example, the highest GOF in a wafer may be 99.5%. The associated CMP characteristics of the target structure with the highest GOF are compared to the CMP design criteria. Similarly, the highest GOF is compared to the optical metrology signal design criteria. If both of the CMP and optical metrology signal design criteria are met 290, the underlying structure associated with target structure with the highest GOF is selected as the underlying structure for the fabrication run. Otherwise, the process proceeds to step 210 to iterate the steps starting with the designing a new set of underlying structures.

Figure 9:
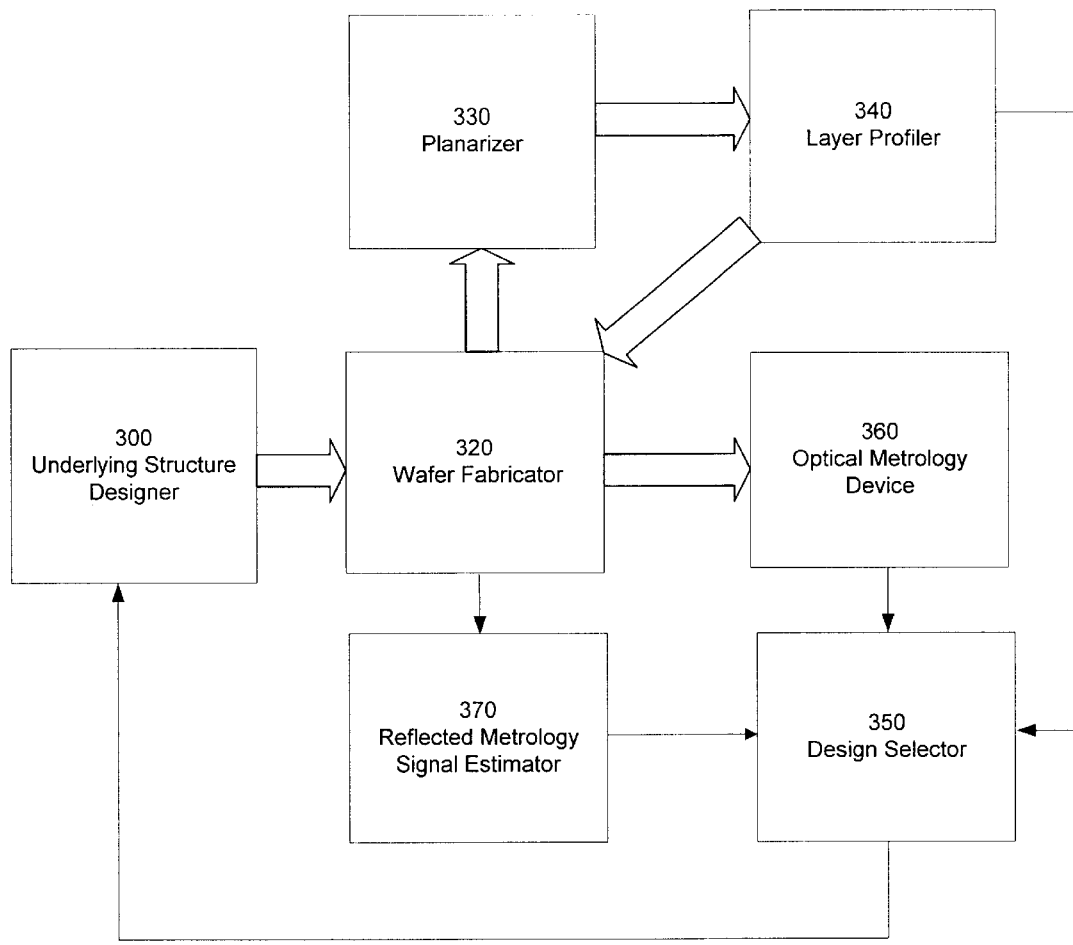
FIG. 9 is an architectural diagram of a system for selecting an underlying structure design that balances planarization and optical metrology objectives in one embodiment of the present invention.

FIG. 9 is an architectural diagram of a system for selecting an underlying structure design that balances planarization and optical metrology objectives in one embodiment of the present invention. An underlying structure designer 300 is used to create designs of underlying structures for a given target structure. The design includes a calibration underlying structure and other underlying structures with varying loading factors and/or line-to-space ratios. The underlying structure design is used in a wafer fabricator 320 to fabricate the underlying structures and layer(s). The wafer is planarized by the planarizer 330 and the planarized surface is measured by a layer profiler 340, sending the planarization characteristics to the design selector 350. An example of the layer profiler is the atomic force profiler mentioned previously. After measurement by the layer profiler 340 of the planarization characteristics, target structures of the target layer of the wafer are fabricated by the wafer fabricator 320. Once the target structures are completed, the calibration test area, an area in the target layer that has an unpatterned underlying layer, is measured using an optical metrology device 360. Other target structures of the target layer are also measured by the optical metrology device 360, with both measurements sent to the design selector 350.

Alternatively, specifications of underlying structure designs from the wafer fabricator 320 may be input into a reflected metrology signal estimator 370 to calculate the reflected signal from the calibration test area and from each of the target structures with either varying loading factors in the case of pads and random shapes or varying line-to-space ratios in the case of periodic structures.

Still referring to FIG. 9, the design selector 350 uses either the calculated or measured reflected metrology signal from the calibration test area and selects the calculated or measured reflected metrology signal from the other target structures that has the highest GOF compared to the calculated or measured reflected metrology signal from the calibration test area. Planarization and metrology characteristics of the selected target structure are compared to the planarization and optical metrology design criteria. If the planarization and optical metrology design criteria are met, then the selected target structure is identified as having an acceptable balance of planarization and optical metrology characteristics. In other words, the underlying structure design improves planarization characteristics of wafer layers while minimizing the introduction, by the underlying structures, of random and/or systematic noise to the reflected optical metrology signal. If the planarization and optical metrology design criteria are not met, then this condition is transmitted to the underlying structure designer 300 such that a new iteration of the process is started for a different design. In addition, an iteration of the process may be done when there is a change in the fabrication process and/or change of fabrication materials.

Figure 10A:
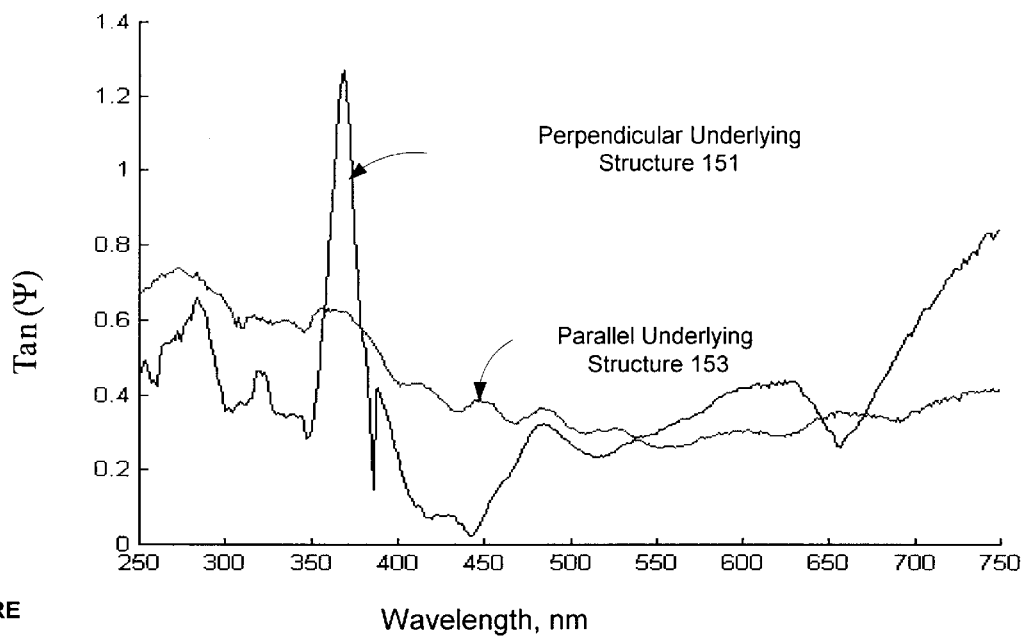
FIG. 10A is a graph of Tan ($\Psi$) versus the wavelength for a parallel underlying structure versus a perpendicular underlying structure in one embodiment of the present invention.
Figure 10B:
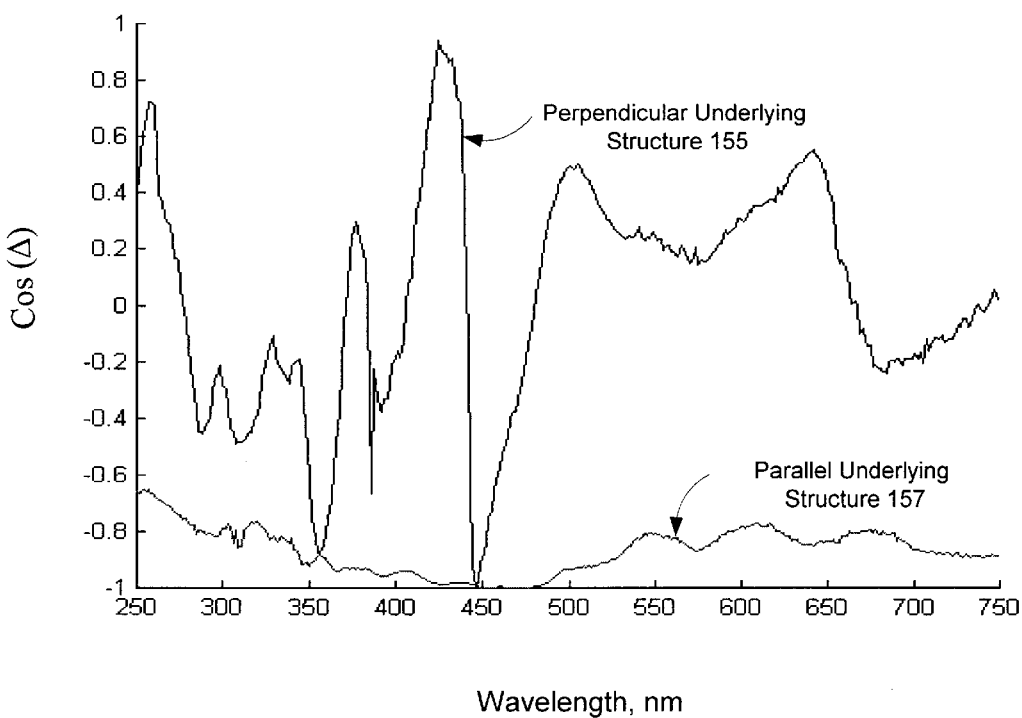
FIG. 10B is a graph of Cos ($\Delta$) versus the wavelength for a parallel underlying structure versus a perpendicular underlying structure in one embodiment of the present invention.

FIG. 10A is a graph of Tan ($\Psi$) versus the wavelength for a parallel underlying structure versus a perpendicular underlying structure in one embodiment of the present invention. The Tan ($\Psi$) versus the wavelength graph 151 of the reflected metrology signal for an underlying structure whose periodicity is perpendicular to the periodicity of the target structure shows a significant number of spikes with big amplitudes. On the contrary, the Tan ($\Psi$) versus the wavelength graph 153 of the reflected metrology signal for an underlying structure whose periodicity is parallel to the periodicity of the target structure shows a small number of spikes with small amplitudes. The two graphs 151 and 153 were obtained by using a constant line-to-space ratio for the underlying structures. Similarly, FIG. 10B is a graph of Cos ($\Delta$) versus the wavelength for a parallel underlying structure versus a perpendicular underlying structure in one embodiment of the present invention. The Cos ($\Delta$) versus the wavelength graph 155 of the reflected metrology signal for an underlying structure whose periodicity is perpendicular to the periodicity of the target structure shows a significant number of spikes with big amplitudes. On the contrary, the Cos ($\Delta$) versus the wavelength graph 157 of the reflected metrology signal for an underlying structure whose periodicity is parallel to the periodicity of the target structure shows a small number of spikes with small amplitudes. The two graphs 155 and 157 were obtained by using a constant line-to-space ratio for the underlying structure. From an optical metrology point-of-view, graphs with more spikes and greater amplitudes are preferred as there is more differentiation of one target structure profile versus another target structure profile.

Foregoing described embodiments of the invention are provided as illustrations and descriptions. They are not intended to limit the invention to precise form described. In particular, it is contemplated that functional implementation of invention described herein may be implemented equivalently in hardware, software, firmware, and/or other available functional components or building blocks.

Other variations and embodiments are possible in light of above teachings, and it is thus intended that the scope of invention not be limited by this Detailed Description, but rather by Claims following.

What is claimed is:

1. A method of designing underlying struck in a wafer that balances planarization and optical metrology characteristics, the method comprising:

fabricating underlying structures including one or more pads the one or more pads varying in size and/or shape;

comparing planarization characteristics of planarized layer or layers of the wafer to preset standard planarization characteristics;

fabricating target structures in the target layer of the wafer;

measuring a reflected metrology signal off a target structure fabricated above a calibration test area of the target layer of the wafer to obtain a calibration metrology signal, the calibration test area having an unpatterned underlying structure; and selecting the design of pads of the underlying structure that yields a reflected metrology signal off the target structure above a patterned area that is closest to the calibration metrology signal and that meet the preset standard planarization characteristics.

2. A method of designing underlying structure in a wafer that balances planarization and optical metrology characteristics, the method comprising:

fabricating underlying structures including one or mote random shapes and one or more spaces, the one or more random shapes varying in size and/or shape;

comparing planarization characteristics of the underlying layers of the wafer to preset standard planarization characteristics;

fabricating target structures in the target layer of the wafer;

measuring a reflected metrology signal off a target structure fabricated above a calibration test area of the target layer of the wafer to obtain a calibration metrology signal, the calibration test area having an unpatterned underlying structure; and selecting an underlying structure of the underlying structures of one or more random shapes that yields a reflected metrology signal off the target structuer above a patterned area that is closest to the calibration metrology signal, the selected underlying structure having planarized layers that meet the preset standard planarization characteristics.

3. A method of designing underlying structures in a wafer that balances planarization and optical metrology characteristics, the method comprising:

fabricating underlying structures with one or more periodic structures, the one or more periodic structures having one or more lines and one or more spaces in one or more underlying layers of a wafer;

comparing planarization characteristics of one or more planarized layers of the wafer to preset standard planarization characteristics;

fabricating target structures in the target layer of the wafer;

measuring a reflected metrology signal off a target structure fabricated above a calibration test area of the target layer of the wafer to obtain a calibration metrology signal, the calibration test area having an unpatterned underlying structure; and selecting an underlying structure of the underlying structures with one or more periodic structures that yields a reflected metrology signal off the target structure above a patterned area that is closest to the calibration metrology signal, the selected underlying structure having one or more planarized layers that meet the preset standard planarization characteristics.

4. The method of designing underlying strokes of claim 3 wherein the underlying structures with one or more periodic structures comprise:

a first periodic underlying structure in a first underlying layer with a predetermined line-to-space ratio, the line-to-space ratio being the ratio of area occupied by the lines to the area occupied by the spaces; and a second periodic underlying structure in a second underlying layer, the second periodic underlying structure having lines covering the spaces of the first periodic underlying structure.

5. The method of designing underlying structures of claim 4 wherein the number of lines of the first underlying structure is 2, 4, or 6.

6. A method of selecting an underlying structure design that balances planarization and optical metrology objectives for a tar get structure, the method comprising:

fabricating underlaying structures in underlying layers of a wafer, the underlying structures designed to balance planarization and optical metrology objectives;

measuring planarization characteristics of the underlying layers of the wafer;

measuring optical metrology characteristics of the target structure; and comparing the planarization characteristics of the underlying layers to the planarization objectives and the optical metrology characteristics of the target structure to the optical metrology objectives, wherein measuring optical metrology characteristics of the target structure further comprises:

calculating a reflected metrology signal from the target structure assuming the underlying layers are unpatterned;

measuring an actual reflected metrology signal from the target structure; and comparing the calculated reflected metrology signal to the actual reflected metrology signal from the target structure.

7. The underlying structure design optimization method of claim 6 wherein the planarization objectives comprise limits on dimensions of dishing and erosion in the underlying planarized layers.

8. The underlying structure design optimization method of claim 6 wherein the optical metrology objectives comprises meeting a predetermined goodness of fit, the goodness of fit being the inverse of the error metric between the calculated reflected metrology signal to the actual reflected metrology signal from the target structure.

9. The underlying structure deign optimization method of claim 6 wherein the underlying structures in the underlying layers of the wafer include pads random shapes, or periodic structures.

10. The method of claim 1 wherein the planarization characteristics of the planarized layers of the wafer comprises measurements of extent of erosion and/or dishing of materials of the planarized layer or layers of the wafer.

11. The method of claim 2 wherein the planarization characteristics of the planarized layers of the wafer comprises measurements of extent of erosion and/or dishing of materials of the planarized layers of the wafer.

12. The method of claim 2 wherein the one or more underlying structures have a loading factor, the loading factor being the ratio of area occupied by one or more random shapes to the erea occupied by both the one or more random shapes and spaces.

13. The method of claim 12 wherein the one or more random shapes include pads with geometric shapes.

14. The method of claim 12 wherein the one or more random shapes include pads with irregular shapes.

15. The method of claim 12 wherein the one or more random shapes include geometric shapes positioned in a random manner.

16. The method of claim 2 wherein the one or more underlying structures in the wafer is a underlying periodic structure, the periodicity of the underlying periodic structure being positioned at an angle relative to the direction of periodicity of the target structure of the wafer.

17. The method of claim 2 wherein the one or more underlying structure in the wafer includes a first layer of underlying periodic structure and a second layer of underlying periodic structure, the periodicity of the first layer of underlying periodic structure, the periodicity of the first layer of underlying periodic structure and the second layer of underlying periodic structure being positioned perpendicular to the direction of periodicity of the target structure of the wafer.

18. The method of claim 17 wherein second layer of underlying periodic structure includes lines and space the spaces being optically transparent to metrology signals.

19. The method of claim 18 wherein the second layer of the underlying periodic structure comprises lines and spaces and the line-to-space ratio ranges from 0.10 to 0.60.

20. The method of claim 18 wherein the number of spaces of the second layer of the underlying structure is 2, 4, or 6.

* * * * *